(12) United States Patent
Tucker et al.

(10) Patent No.: US 11,724,099 B1
(45) Date of Patent: Aug. 15, 2023

(54) SEMI-DRY ELECTRODE FOR A NEURAL SENSOR NET

(71) Applicant: Brain Electrophysiology Laboratory Company, LLC, Eugene, OR (US)

(72) Inventors: Don M. Tucker, Eugene, OR (US); Easwara Moorthy Essaki Arumugam, Eugene, OR (US)

( * ) Notice: Subject to any disclaimer, the term of this patent is extended or adjusted under 35 U.S.C. 154(b) by 0 days.

(21) Appl. No.: 17/888,614

(22) Filed: Aug. 16, 2022

(51) Int. Cl.
  *A61N 1/04* (2006.01)

(52) U.S. Cl.
  CPC .............. *A61N 1/04* (2013.01); *A61N 1/044* (2013.01); *A61B 2562/0217* (2017.08)

(58) Field of Classification Search
  CPC .................................. A61N 1/04; A61N 1/044
  See application file for complete search history.

(56) References Cited

U.S. PATENT DOCUMENTS

| | | | | |
|---|---|---|---|---|
| 2017/0135596 | A1* | 5/2017 | Fan ........................ | A61B 5/291 |
| 2020/0022605 | A1* | 1/2020 | Lee ........................ | A61B 5/291 |
| 2022/0162765 | A1* | 5/2022 | Pain ....................... | B33Y 10/00 |

FOREIGN PATENT DOCUMENTS

CN  106419913 A  * 2/2017

OTHER PUBLICATIONS

Guang Li-Li et al., "Review of semi-dry electrodes for EEG recording," Journal of Neural Engineering 17, Oct. 21, 2020, pp. 1-26.

* cited by examiner

*Primary Examiner* — Joseph M Dietrich
(74) *Attorney, Agent, or Firm* — Garth Janke, LLC (57) ABSTRACT

A semi-dry electrode for a neural sensor net. The electrode may comprise an electrolyte storage medium for storing electrolyte, a body portion including an electrolyte reservoir for receiving the bottom surface of the electrolyte storage medium, a cap connected to the body portion for at least partially covering the top surface of the electrolyte storage medium so as to prevent contact between the top surface of the electrolyte storage medium and a person's finger(s), and a vibrating device for vibrating the electrode so as to release electrolyte from the electrolyte storage medium out through the body portion.

10 Claims, 8 Drawing Sheets

SEMI-DRY ELECTRODE FOR A NEURAL SENSOR NET

FIELD OF INVENTION

The present invention relates generally to neural sensor nets, which are used to position electrodes on the surface of the head, and which may be used for either or both brain measurement, such as electroencephalography (EEG), and brain stimulation, such as transcranial electrical stimulation (TES). More particularly, the invention relates to an electrode for a neural sensor net, and more particularly still, to electrodes that are, to a limited extent, wetted with electrolyte.

BACKGROUND

Electrodes are electrical conductors, and are used in neural sensor nets either or both for measuring electrical potentials on the scalp, arising from brain activity, or injecting electrical current into the brain through the scalp, to stimulate brain activity. There are well known barriers to make good electrical contact with the skin, such as dead skin cells and the poor electrical conductivity of natural skin oil. Especially since electrical activity in the brain is also inherently difficult either to monitor or control precisely from the scalp, it is important that the electrodes of a neural sensor net make good and controlled electrical contact with the skin of the scalp.

To help assure this, electrodes of neural sensor nets are typically applied over an electrolyte which is typically a gel, to act as an electrically conductive "bridge" from the electrode to the skin on the scalp. Following terminology used in the art, the use of an electrolyte transforms what would otherwise be called a "dry" electrode to which no electrolyte has been added, into a "wet" electrode.

Sometimes a sponge is provided, the electrolyte is soaked into the sponge, and the sponge is disposed between the electrode and the skin, as an intermediating element. In this case the electrolyte may be either a liquid or a gel. Again following terminology in the art, the use of a sponge or other electrolyte storage medium, which limits the amount of electrolyte that can be first absorbed and thereafter released by the electrode, transforms a "dry" electrode into a type generally referred to as "semi-dry."

Semi-dry electrodes bridge the gap between typical wet and dry electrodes, retaining the advantages of both while addressing most of their respective drawbacks. Typically, the volume of electrolyte in a semi-dry electrode is approximately a few tens of microliters, which is substantially less than that of conductive gels (1-2 ml) used for wet electrodes. With such small amounts of electrolyte, semi-dry electrodes not only avoid dirtying the hair and prevent short circuits, but can also locally hydrate the scalp, thereby reducing the electrode/scalp impedance and effectively coupling the electrode to the scalp.

The present invention is directed to improvements in the art of semi-dry electrodes.

SUMMARY

Disclosed is a semi-dry electrode for a neural sensor net. The electrode may comprise an electrolyte storage medium for storing electrolyte, the electrolyte storage medium having opposed top and bottom surfaces; a body portion including an electrolyte reservoir for receiving the bottom surface of the electrolyte storage medium; a cap connected to the body portion for at least partially covering the top surface of the electrolyte storage medium so as to prevent contact between the top surface of the electrolyte storage medium and a person's finger(s); and a vibrating device for vibrating the electrode so as to release electrolyte from the electrolyte storage medium out through the body portion.

All of the following features of the semi-dry electrode may be provided separately or together in any combination.

The cap may be configured for repeatedly connecting to and disconnecting from the body portion.

The cap may have holes allowing electrolyte to substantially freely enter the electrolyte reservoir.

The electrolyte reservoir may comprise a sponge.

The electrolyte reservoir may comprise one or more capillary tubes.

The electrolyte storage medium may have one or more side surfaces, and the body portion may be adapted for enclosing the one or more side surfaces.

The vibrating device need not be attached to the electrode.

The body portion may comprise a plurality of spaced apart legs for standing the remainder of the electrode away from the skin.

The legs may be hollow and the body portion may be adapted to allow electrolyte from the electrolyte reservoir to flow through the interiors of the legs.

The body portion may be adapted to allow the electrolyte to flow along outer surfaces of the legs.

Also disclosed is a method for semi-dryly wetting an electrode in a neural sensor net. The method may comprise providing an electrolyte storage medium; storing electrolyte in the electrolyte storage medium; and vibrating the electrode at a frequency of at least 5 Hz, thereby releasing some or all of the electrolyte stored in the electrolyte storage medium.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

BRIEF DESCRIPTION OF DRAWINGS

Note that all the drawings are to scale.

DESCRIPTION OF PREFERRED EMBODIMENTS

The present inventors have recognized a problem with the prior art methods of providing electrolyte for use with a neural sensor net. That is, it is difficult to avoid wetting the skin and hair on the scalp with electrolyte to such an extent that it not only forms an electrically conductive "bridge" to the skin underneath the electrode under which it is provided, but it also forms an electrically conductive bridge to adjacent electrodes. Thus an electrode may interfere with the electrical signal or transmission integrity of neighboring electrodes.

It is not practical for a person to apply a neural sensor net to the head of a subject without touching any of the electrodes, and just touching an electrode that is seated on a sponge soaked with electrolyte can be enough to release too much electrolyte to the environment surrounding the electrode. To solve this problem, the present inventors have arrived at a method that will not release electrolyte unless and until the electrodes are specially agitated.

Figure 1:
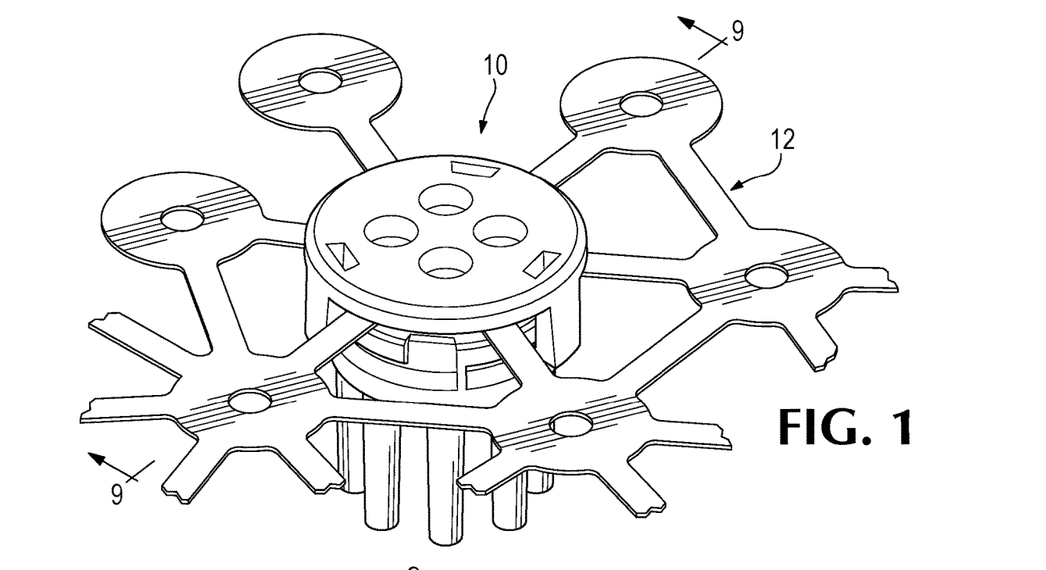
FIG. 1 is an isometric upper side view of a first preferred semi-dry electrode for a neural sensor net according to the present invention.
Figure 2:
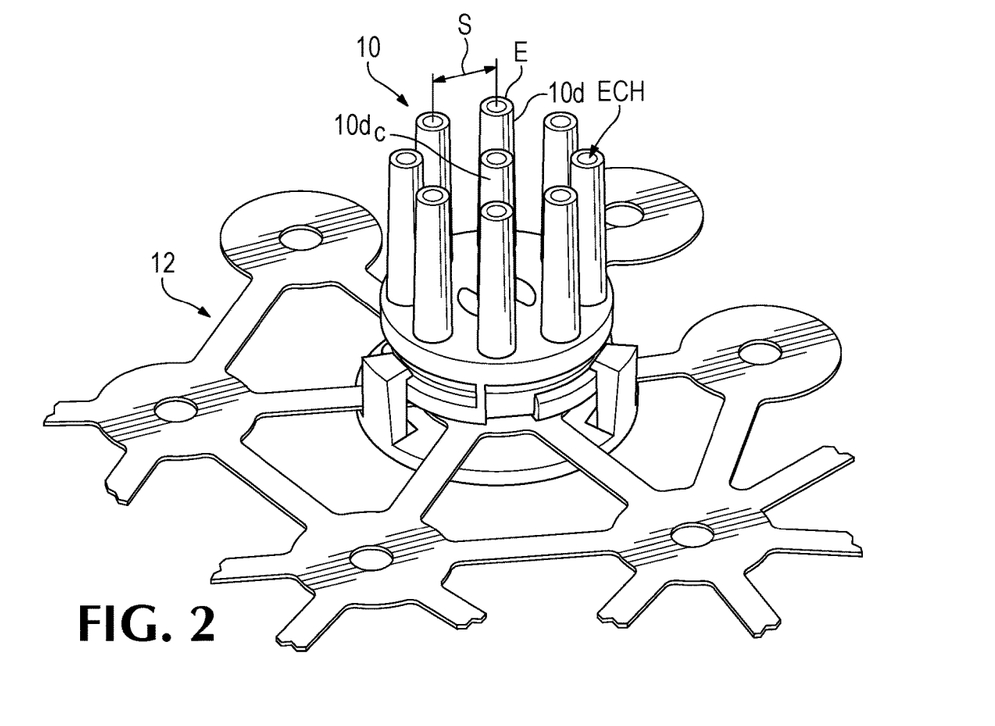
FIG. 2 is an isometric lower side view of the electrode and sensor net of FIG. 1.

FIGS. 1 and 2 show a first preferred electrode 10 according to the present invention for such use. The electrode 10 is shown attached to a flexible net 12, which may be die-cut from a flexible sheet of a plastic or silicone material; preferably an elastomer such as thermal polyurethane. The manner of attachment is evident from FIGS. 3 and 4. In particular, with reference to these latter Figures, a cap portion 10a of the electrode 10 may have prongs 13 with protrusions 13a at their ends, the protrusions 13a extending inwardly, toward a central axis "CA" of the electrode 10. The protrusions 13a may be passed through corresponding slots 14a in a body portion 10b of the electrode 10, and then the cap portion 10a may be twisted relative to the body portion 10b so that the protrusions will grip the undersides "US" (FIG. 4) of annular ledge portions 14b of the body portion 10b, thereby securing the cap portion 10a to the body portion 10b, as means for repeated connection and disconnection between the cap portion 10a and the body portion 10b. Equivalently, protrusions could be provided on the body portion 10b and ledges on the cap portion 10a. And of course, many alternative provisions could be made to provide this common function, including protrusions on either one of these two elements that "snap fit" into corresponding depressions in the other.

The body portion 10b of the electrode 10 is intended to make physical and electrical contact with the scalp, particularly at ends "E" of legs 10d. The body portion may be formed of any suitable electrically conductive material, which is typically an electrically conductive polymer, which may be formed in one piece such as by injection molding. The cap portion 10a may be formed of the same or different material or materials, and need not be electrically conductive.

Preferably there are a plurality of legs 10d, spaced apart from each other (spacing "S" in FIG. 2), and the ends E of the legs 10d preferably lie in substantially the same plane, so that all of the ends can make contact with the scalp. Preferably there are at least eight of the legs 10d, which are preferably arranged in a circle, but neither of these conditions is essential.

Figure 3:
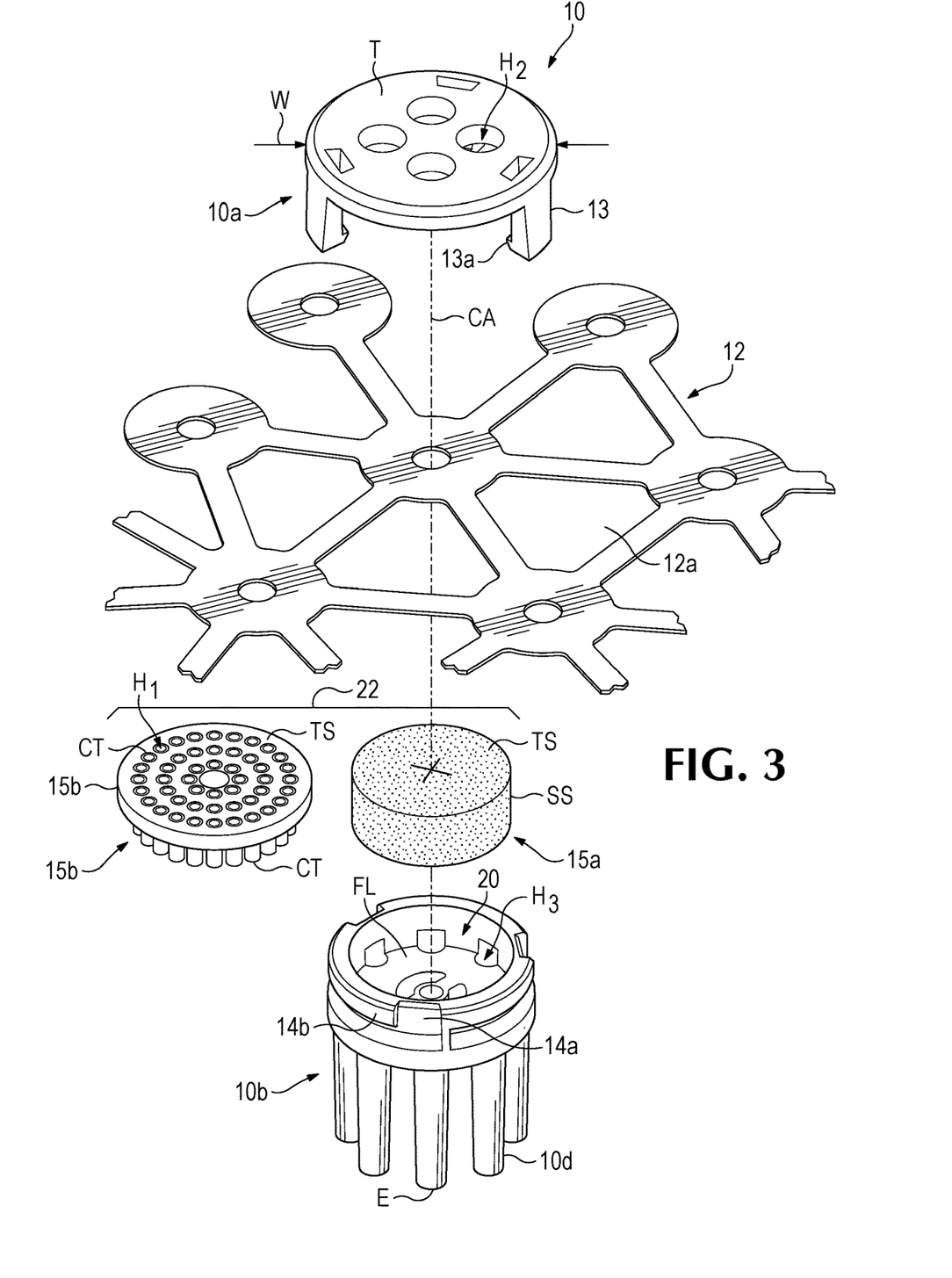
FIG. 3 is an isometric upper side exploded view of the electrode and sensor net of FIG. 1.

Referring to FIG. 3, the electrode 10 has a maximum diameter or width (because although they are typically circular this is not essential) "W" centered on the axis CA of about 5 to 15 mm (or about 0.2 to 0.6 inches). The electrodes 10 are small; there are typically over 500 of them on the net 12.

Preferably, at least the ends E of the legs 10d are substantially smaller than the width W, e.g., by a factor of 5-10, to increase the pressure they exert on the scalp and thereby helping them to burrow through hairs, with the spacing S between the legs 10d providing space for the hairs so that the electrodes are better able to avoid the hairs and make contact with the skin.

Staying with FIG. 3, the electrode 10 has an electrolyte reservoir 20 that is spaced proximally away from the ends E of the legs 10d. In preferred embodiments, this reservoir includes a removable electrolyte storage medium 22 (two alternatives are shown), which may be a sponge 15a or a capillary tube assembly 15b with capillary tubes "CT" oriented, preferably, parallel to the axis CA. The sponge or capillary tube assembly as the case may be retains the electrolyte which may be liquid or gel, by capillary attraction to the pores or interior surfaces thereof.

Figure 4:
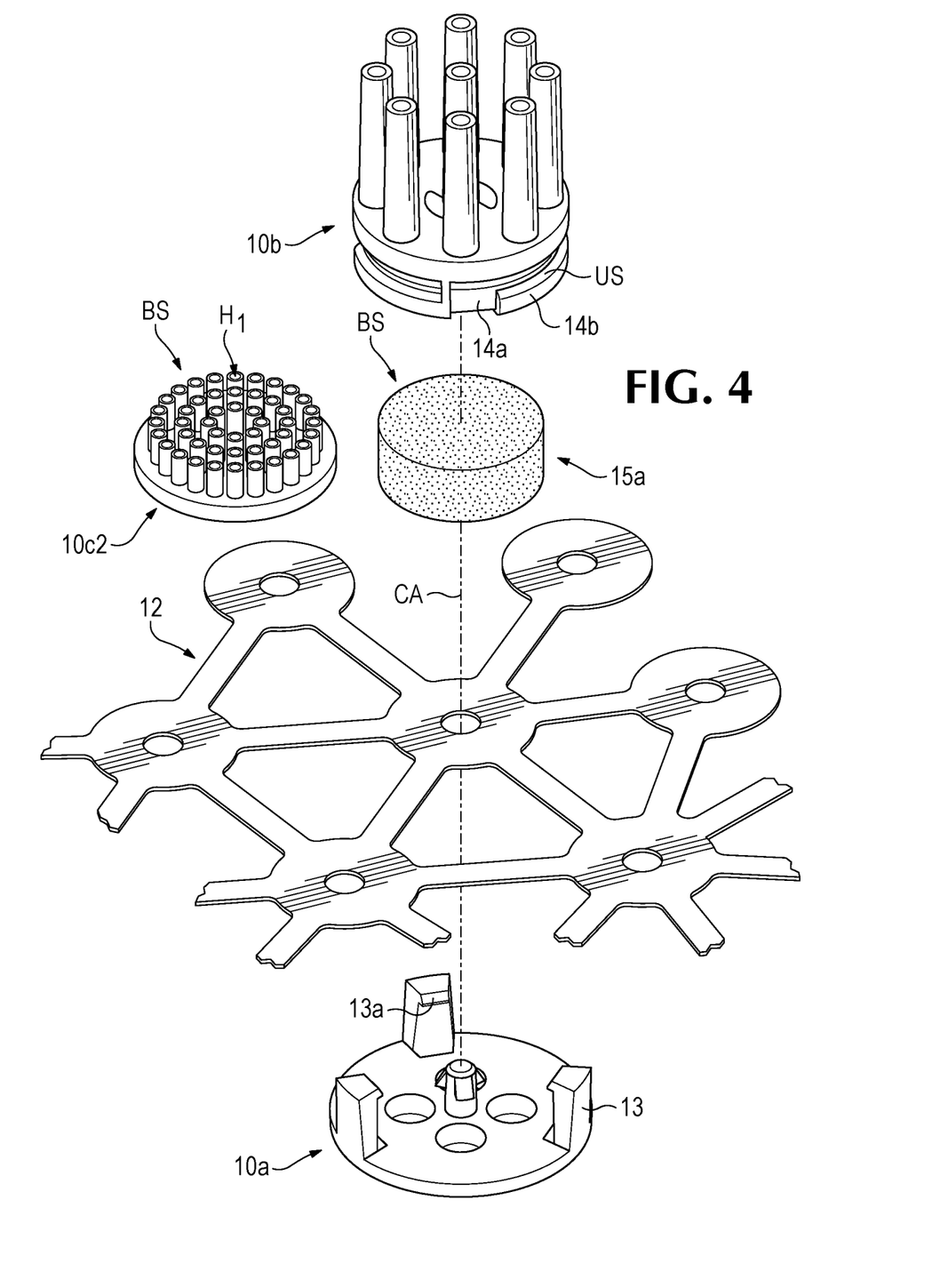
FIG. 4 is an isometric lower side exploded view of the electrode and sensor net of FIG. 1.
Figure 5:
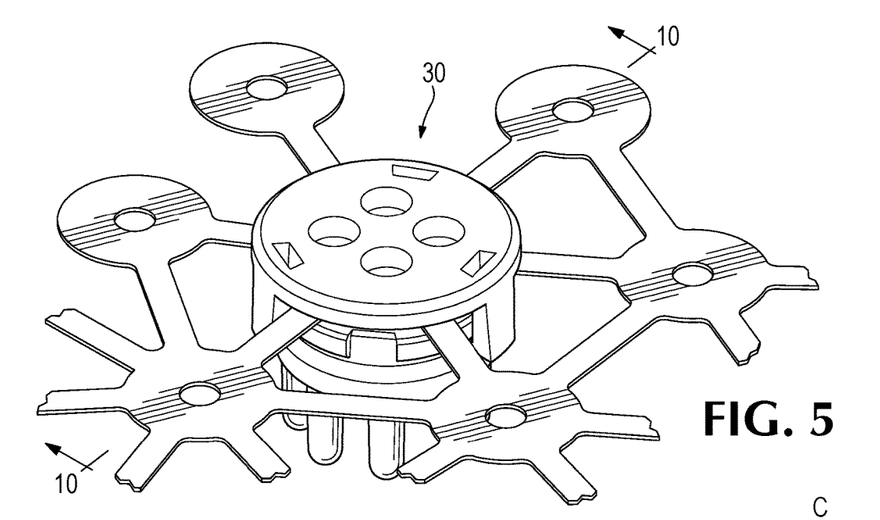
FIG. 5 is an isometric upper side view of a second preferred semi-dry electrode for a neural sensor net according to the present invention.

The sponge 15a generally has a top surface "TS," a side surface "SS," and, with reference to FIG. 4, a bottom surface "SS." And the same is true for the capillary tube assembly 15b, except that the capillary tubes in the capillary tube assembly have respective holes "$H_1$," extending therethrough. The electrolyte reservoir in the body portion 10b typically and preferably receives both the bottom and side surfaces of the electrolyte storage medium, however leaving the top surfaces exposed, with the top surfaces being covered by the cap portion 10a, so that the electrolyte storage medium is fully contained within the electrode when the cap portion 10a is attached to the body portion 10b.

For best results, the electrolyte should behave as a liquid as opposed to a gel, the latter being mostly liquid in content but behaving like a solid due to cross-linking. As one example, the electrolyte may be a saline solution (water+ sodium chloride) mixed with 40%-80% glycerine or glycerol by volume, and the assembled electrodes 10 may be dipped into a bath of the electrolyte to store a portion of the electrolyte in the electrolyte reservoir 20 before the net is applied to the head. In such case electrolyte may enter the reservoir 20 through holes "$H_2$" in the cap portion 10a. Alternatively and/or to replenish the electrolyte reservoir 20 while the net is on the head a roller, similar to a paint roller, that is soaked with electrolyte may be run across the tops "T" of the cap portions 10a and, again, enter the reservoir through the holes $H_2$.

The cap portion 10a protects the electrolyte storage medium 22 from being touched as the net 12 is being applied, and as a consequence protects against releasing electrolyte before that is desired. When the net has been finally positioned on the scalp, the user can release the electrolyte from the storage medium 22 by stimulating the tops T of the cap portions 10a with a vibrating device (not shown), such as that marketed as the DynaMini Massage Gun by Lifepro Fitness LLC of Eatontown, N.J.

The vibrating device may be simply held in the hand, or it may be worn on the body such as on the hand, arm, or shoulder. The device may have a vibrating head which may be applied to contact the tops of the electrodes, or the device may simply be used to cause the hand or other part of the body to vibrate, and the hand (or other part of the body) may be used to contact the tops of the electrodes.

The vibrating device could also be miniaturized and made part of or be attached to the electrode itself. For example, it could be a piezoelectric device.

The frequency range of vibration provided by the vibrating device may be about 5-300 Hz, and the amplitude of vibration may be about a tenth to a quarter of a millimeter (or about 4-10 thousandths of an inch).

Such agitation has been found to work well for releasing electrolyte from the electrolyte storage medium 22 in both the sponge and capillary tube assembly embodiments. In the embodiment 10, the legs 10d are hollow, so that the agitation may release the electrolyte from the sponge, or from the holes $H_1$ through the capillary tubes in the capillary tube assembly, into the hollows of the legs, through holes "$H_3$" in a floor "FL" of the electrode leading to the hollows in the legs, so that the electrolyte is free to flow through the interiors of the legs and out through the open ends E of the legs onto the skin.

Assuming a cylindrically shaped electrolyte conduction hole "ECH" (FIG. 2) through the legs 10d for conducting the electrolyte, the inner diameter of the hole is about 1 mm+/−20%, and for hole shapes that are not cylindrical, a comparable average effective diameter can be used. The outer diameter or average effective diameter of the legs may be about 3 mm+/−50%, and the number of legs can vary between 1 and 10. These dimensions assume again an electrolyte with glycerine or glycerol in the percentage range indicated above, suitable for optimizing the balance between capillary attraction and the force of gravity.

FIGS. 5-8 correspond to FIGS. 1-4 respectively, showing a second preferred electrode 30 according to the present invention. The difference in this embodiment is that legs 30d, corresponding to the legs 10d of the electrode 10 (compare FIGS. 2 and 6A) have closed rather than open ends E, so that electrolyte does not flow through the legs. In this embodiment, the legs provide the function of parting the hairs of the scalp as noted above, but do not provide the function of releasing electrolyte. Instead, the holes $H_3$ may be repositioned as desired to allow the electrolyte to drop from the floor FL of the reservoir onto the scalp.

Figure 7:
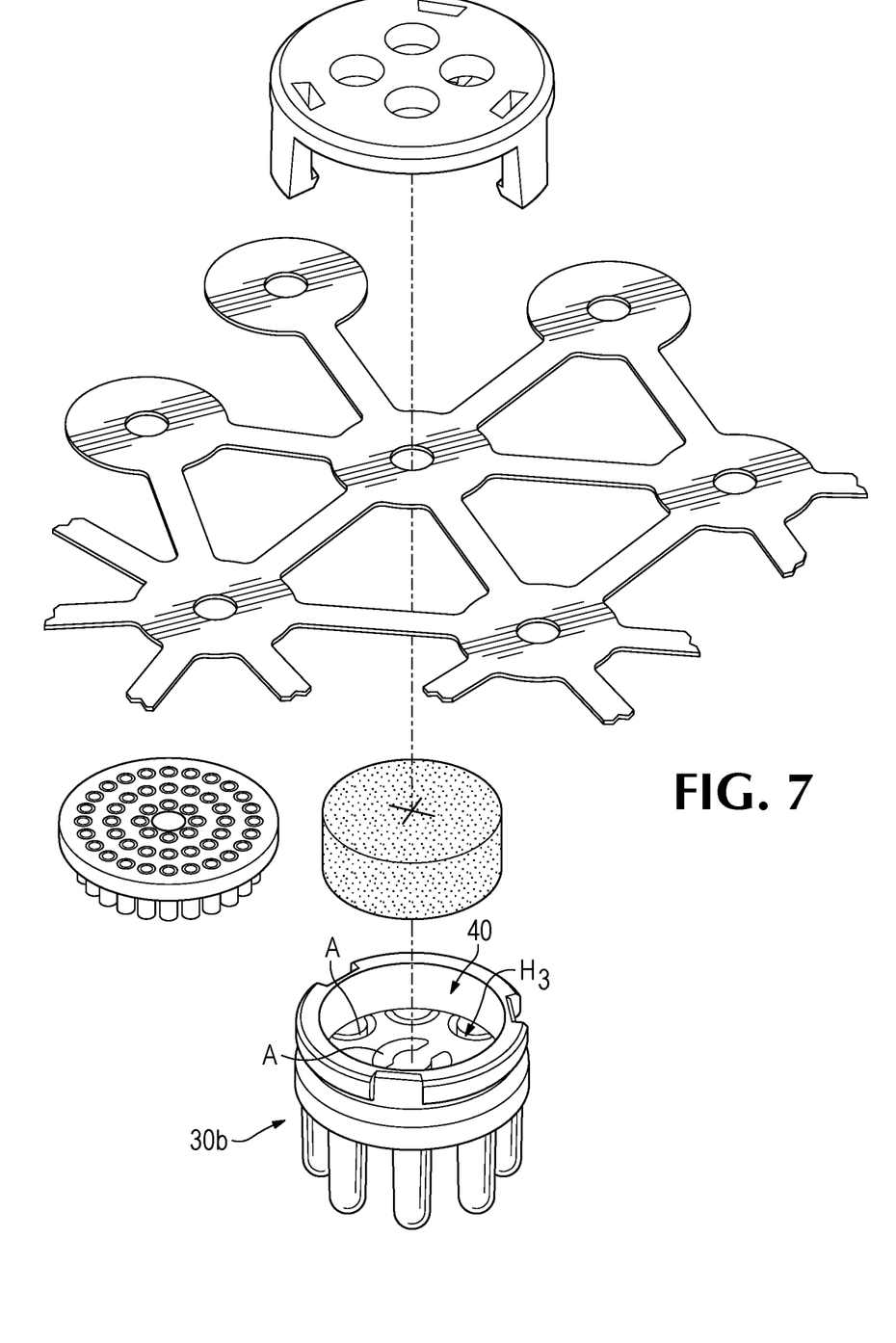
FIG. 7 is an isometric upper side exploded view of the electrode and sensor net of FIG. 5.
Figure 8:
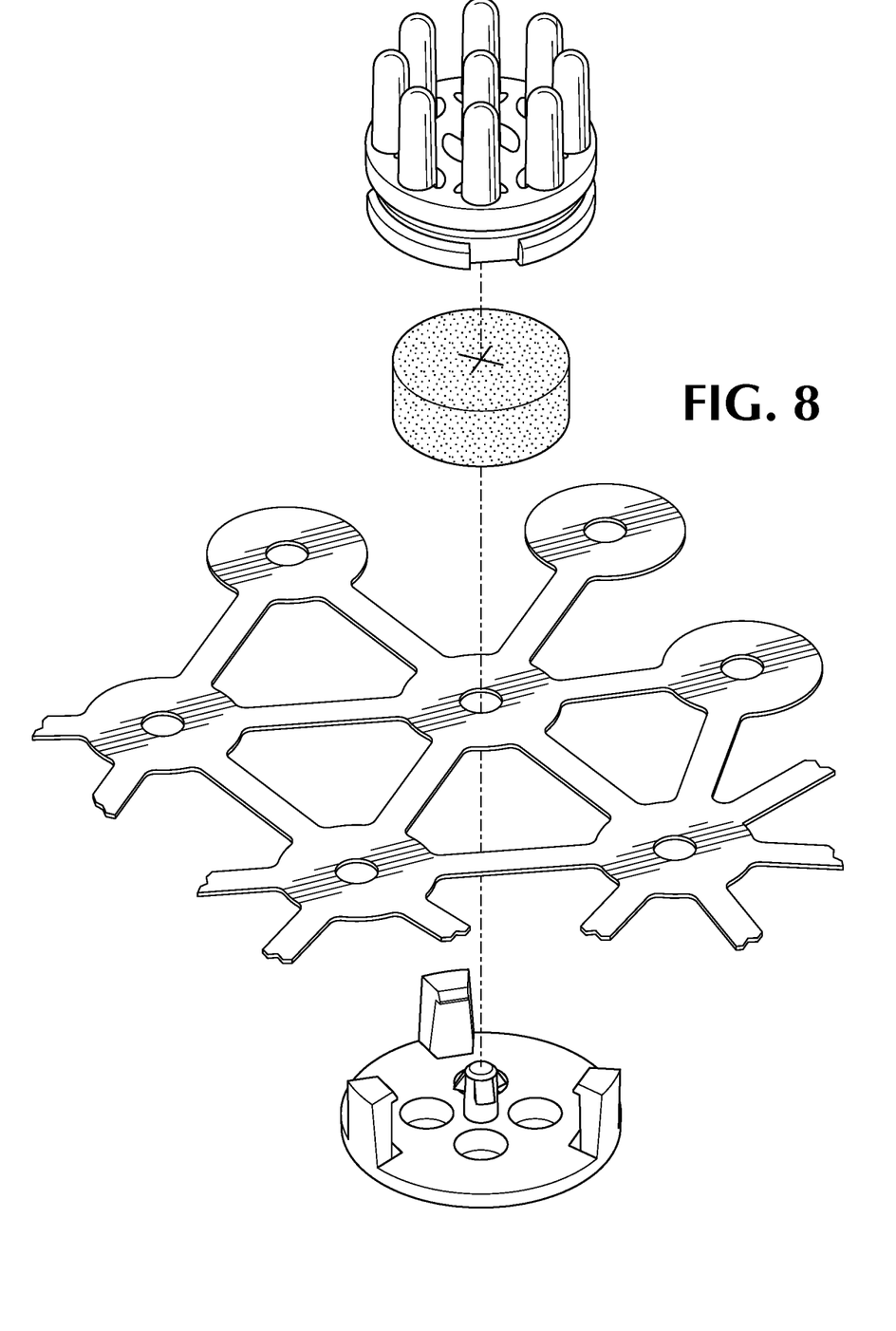
FIG. 8 is an isometric lower side exploded view of the electrode and sensor net of FIG. 5.

The locations of the holes $H_3$ as shown in FIGS. 3 and 7 are suited particularly to conducting the electrolyte along the outside surfaces of the legs, to which the electrolyte may be somewhat capillary attracted, which may provide some advantage in localizing the dispensation of the electrolyte to within the footprint of the electrode.

In particular this provision employs an electrolyte reservoir 40 (FIG. 7), corresponding to the electrolyte reservoir 20 of the electrode 10, that has semi-circular (in this example) apertures "A" that allow electrolyte to flow, by capillary attraction, to exterior surfaces of the legs 30d, after which the electrolyte flows down those exterior surfaces, to which they remain attracted by capillary attraction, under the influence of gravity.

Figures 6A, 6B:
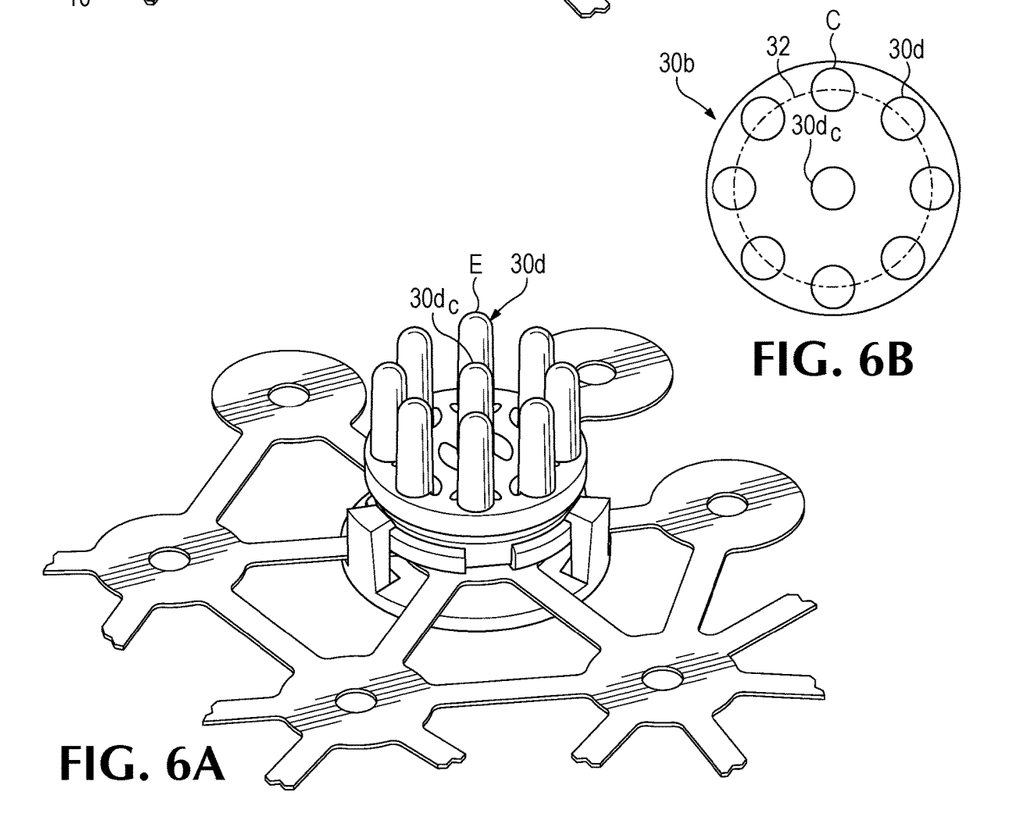
FIG. 6A is an isometric lower side view of the electrode and sensor net of FIG. 5.
FIG. 6B is a bottom plan view of the electrode of FIG. 5.

With reference to FIG. 6B, the apertures A are such that the leg surfaces to which the electrolyte is attracted are inside the reference "circle" 32, which is a true circle in this example but which could be other shapes depending on how the legs 30d are distributed, passing through center points "C" of the legs as the body portion 30b is viewed in plan. This helps to contain the electrolyte within the footprint of the body portion 30b and thereby prevent spill-over to adjacent electrodes.

With reference to FIGS. 2 and 6, note that in the preferred electrodes 10 and 30 there are center legs $10d_c$ and $30d_c$ respectively. With particular reference to FIG. 6 the body portion 30b of the electrode 30 has semi-circular (again, in this example) center apertures $A_c$ that may substantially surround the center leg $30d_c$, so that electrolyte may run down substantially the entire exterior surface of the center leg, which is entirely within the reference circle 32, rather than running down only those portions of the exterior surfaces of the legs around the periphery of the body portion 10b that are within the reference circle 32.

The aforementioned agitation has been found to work the electrolyte running down the legs 30d under the ends E of this embodiment, even though they are closed and no electrolyte flows through these ends as in the embodiment 10, without additional provision for applying the electrolyte to these ends being necessary.

Figure 9:
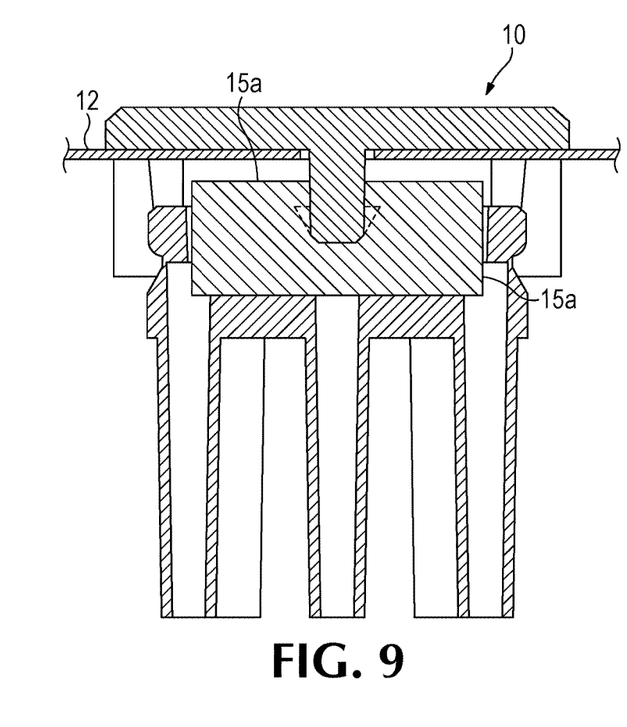
FIG. 9 is a side sectional view of the electrode and sensor net of FIG. 1, with an electrolyte storage medium embodied in a sponge.
Figure 10:
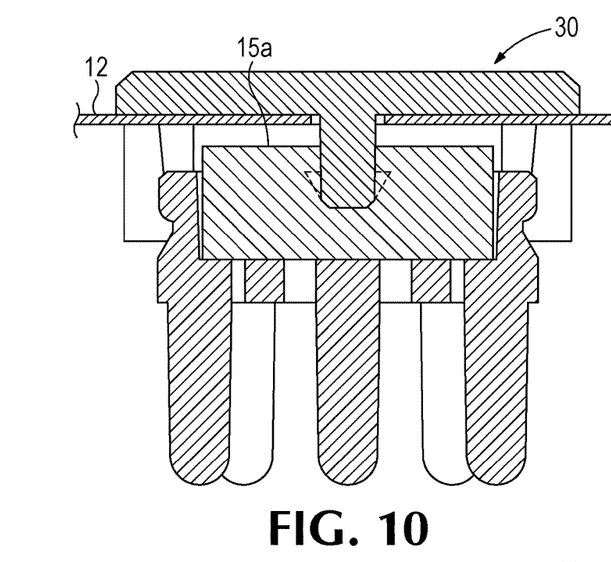
FIG. 10 is a side sectional view of the electrode and sensor net of FIG. 5, with an electrolyte storage medium embodied in a sponge.

FIGS. 9 and 10 are cross-sectional views of the electrodes 10 and 30, respectively, showing the sponge 15a as the electrolyte storage medium 22.

Figure 11:
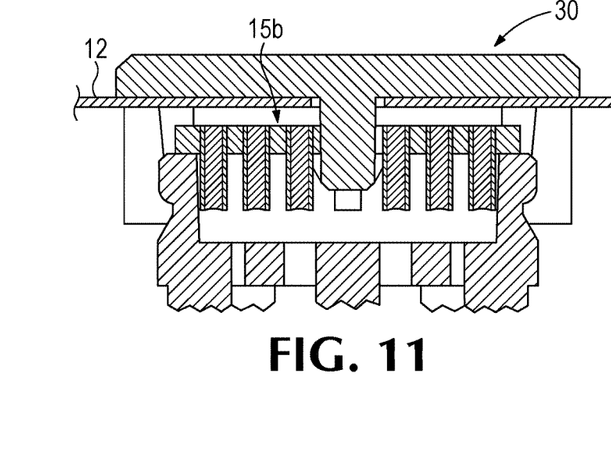
FIG. 11 is a side sectional view of either of the electrodes of FIGS. 1 and 5, with the electrolyte storage medium embodied in a capillary disc.

FIG. 11 is a similar cross-sectional view showing either of the electrodes 10 and 30 with the capillary tube assembly 15b.

Figure 12:
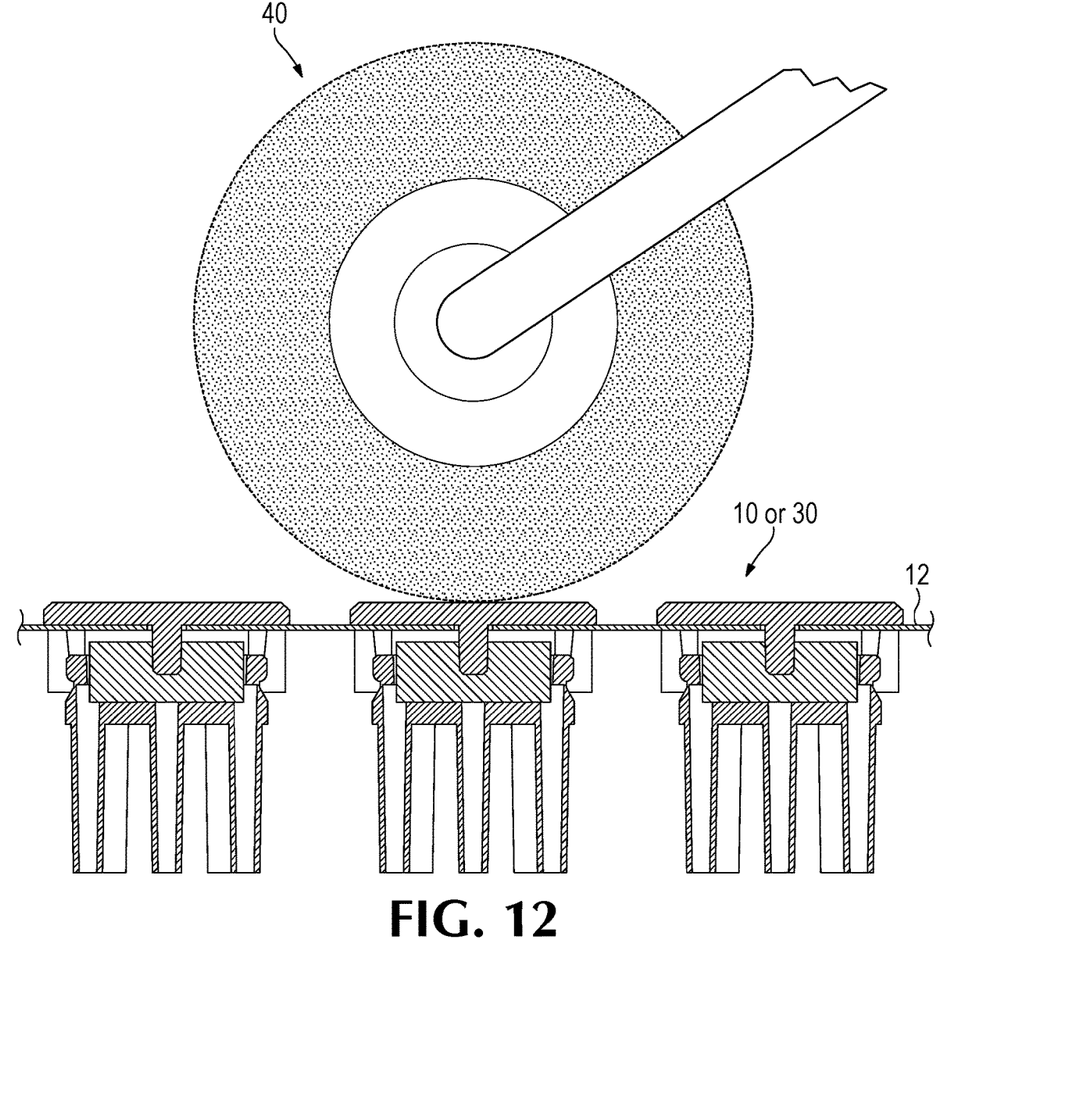
FIG. 12 is a side sectional view of three of the electrodes of FIGS. 1 and 5, showing an applicating roller for supplying electrolyte to the electrodes.

It was noted above that the electrodes may be submerged in a bath of the selected electrolyte, to "fill" or stock the electrolyte storage medium before the electrodes are positioned on the head. FIG. 12 shows an alternative, of applying the electrolyte to the tops of the electrodes with an absorbent (e.g., foam or sponge) electrolyte application roller 40, such as a 3" foam trim paint roller, an example of which is the foamPRO® trim roller supplied by foamPRO® Mfg., Inc. of Irvine, Calif. This alternative method has the advantage of allowing for conveniently replenishing electrolyte in electrodes that have already been positioned on the head.

The electrolyte application roller can be used to add electrolyte to the electrodes after the electrodes are placed on the head, to provide electrolyte to the electrodes in the first place, and/or to replenish electrolyte that has been lost from the electrodes during use. The electrolyte may be absorbed by the roller from a source of electrolyte (e.g., stored in a bucket) and then with gentle pressure rolled over the electrodes. The electrolyte may then flow into the electrolyte reservoir 20 or 40 through the holes H under the influence of gravity.

It is to be understood that, while a specific wet electrode for a neural sensor net has been shown and described as preferred, other configurations could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A semi-dry electrode for a neural sensor net comprising:
    an electrolyte storage medium for storing electrolyte, the electrolyte storage medium having opposed top and bottom surfaces;
    a body portion including an electrolyte reservoir for receiving the bottom surface of the electrolyte storage medium;
    a cap connected to the body portion for at least partially covering the top surface of the electrolyte storage medium so as to prevent contact between the top surface of the electrolyte storage medium and a person's finger(s); and a vibrating device for vibrating the electrode so as to release electrolyte from the electrolyte storage medium out through the body portion.

2. The electrode of claim 1, where in the cap is configured for repeatedly connecting to and disconnecting from the body portion.

3. The electrode of claim 1, wherein the electrolyte reservoir comprises a sponge.

4. The electrode of claim 1, wherein the electrolyte reservoir comprises one or more capillary tubes.

5. The electrode of claim 1, wherein the cap has holes allowing electrolyte to substantially freely enter the electrolyte reservoir.

6. The electrode of claim 1, wherein the electrolyte storage medium has one or more side surfaces, and wherein the body portion is adapted for enclosing the one or more side surfaces.

7. The electrode of claim 1, wherein the vibrating device is not attached thereto.

8. The electrode of claim 1, wherein the body portion comprises a plurality of spaced apart legs and wherein the electrode as a whole therefore comprises the spaced apart legs and remaining portions of the electrode comprising all the other elements recited in claim 1. the spaced apart legs for standing the remaining portions of the electrode away from the skin.

9. The electrode of claim 8, wherein the legs include hollow portions and the body portion is adapted to allow electrolyte from the electrolyte reservoir to flow through the hollow portions of the legs.

10. The electrode of claim 8, wherein the body portion is adapted to allow electrolyte to flow along outer surfaces of the legs.

* * * * *